United States Patent
Elliott

(10) Patent No.: US 7,795,460 B2
(45) Date of Patent: Sep. 14, 2010

(54) METHOD OF MAKING ALKYL ESTERS

(75) Inventor: Brian Elliott, Wheat Ridge, CO (US)

(73) Assignee: TDA Research, Inc., Wheat Ridge, CO (US)

(*) Notice: Subject to any disclaimer, the term of this patent is extended or adjusted under 35 U.S.C. 154(b) by 388 days.

(21) Appl. No.: 11/381,924

(22) Filed: May 5, 2006

(65) Prior Publication Data

US 2007/0260077 A1   Nov. 8, 2007

(51) Int. Cl.
*C11B 1/00* (2006.01)

(52) U.S. Cl. .................................... 554/167

(58) Field of Classification Search ................ 554/174
See application file for complete search history.

(56) References Cited

U.S. PATENT DOCUMENTS

| | | |
|---|---|---|
| 1,967,319 A | 7/1934 | Moore et al. |
| 2,400,607 A | 5/1946 | Segessemann |
| 4,218,386 A | 8/1980 | Logan |
| 4,698,186 A | 10/1987 | Jeromin et al. |
| 5,525,126 A | 6/1996 | Basu et al. |
| 5,713,965 A | 2/1998 | Foglia et al. |
| 5,908,946 A | 6/1999 | Stern et al. |
| 6,147,196 A | 11/2000 | Stern et al. |
| 6,399,800 B1 | 6/2002 | Haas et al. |
| 6,712,867 B1 | 3/2004 | Boocock |
| 6,768,015 B1 | 7/2004 | Luxem et al. |
| 6,855,838 B2 | 2/2005 | Haas et al. |
| 6,887,283 B1 | 5/2005 | Ginosar et al. |
| 6,965,044 B1 | 11/2005 | Hammond et al. |
| 7,090,788 B2 | 8/2006 | Elliott |
| 7,122,688 B2 | 10/2006 | Lin et al. |
| 7,211,681 B2 | 5/2007 | Furuta et al. |
| 2003/0158074 A1* | 8/2003 | Haas et al. ............. 510/458 |
| 2004/0034244 A1 | 2/2004 | Bournay et al. |

(Continued)

FOREIGN PATENT DOCUMENTS

WO   WO 81/00846   4/1981

OTHER PUBLICATIONS

Chem. Abstr. of KR 2002028120, Apr. 16, 2002.*

(Continued)

*Primary Examiner*—Deborah D Carr
(74) *Attorney, Agent, or Firm*—Greenlee, Winner and Sullivan, P.C.

(57) ABSTRACT

Methods of making alkyl esters are described herein. The methods are capable of using raw, unprocessed, low-cost feedstocks and waste grease. Generally, the method involves converting a glyceride source to a fatty acid composition and esterifying the fatty acid composition to make alkyl esters. In an embodiment, a method of making alkyl esters comprises providing a glyceride source. The method further comprises converting the glyceride source to a fatty acid composition comprising free fatty acids and less than about 1% glyceride by mass. Moreover, the method comprises esterifying the fatty acid composition in the presence of a solid acid catalyst at a temperature ranging firm about 70° C. to about 120° C. to produce alkyl esters, such that at least 85% of the free fatty acids are converted to alkyl esters. The method also incorporates the use of packed bed reactors for glyceride conversion and/or fatty acid esterification to make alkyl esters.

24 Claims, 2 Drawing Sheets

Reaction of ethanol and hexanoic acid over Amberlyst-15 in a packed bed catalytic reactor
(5:1) ethanol : hexanoic aicd

U.S. PATENT DOCUMENTS

2005/0107624 A1     5/2005   Lin et al.
2006/0069274 A1*    3/2006   Dias De Moraes E Silva et al.
........................................................................ 554/174
2006/0293533 A1     12/2006   Iyer

OTHER PUBLICATIONS

Kiss et al., Adv. Synth. Catal., 2006, pp. 75-81.*
Mbaraka et al., JAOCS, vol. 83, No. 2, 79-90.*
Steinigeweg et al., Ind. Eng. Chem. Res., 2003, vol. 42, pp. 3612-3619.*
Canakci, M., et al., "Biodiesel Production Via Acid Catalysis," Transactions of the ASAE, 1999, pp. 1203-1210, vol. 42, No. 5, American Society of Agricultural Engineers.
Patent application entitled "Methods of Making Alkyl Esters" by Brian Elliott, filed May 4, 2007 as U.S. Appl. No. 11/744,693.
Xu et al., Heterogeneous Catalysis Using a Nanostructured Solid Acid Resin Based on Lyotropic Liquid Crystals, J. Am. Chem. Soc. 2004, 126, 1616-1617.
Standard Test Method for Acid Value of Fatty Acids and Polymerized Fatty Acids; Designation: D 1980-87 (Reapproved 1998); American Society for Testing and Materials.
Xu et al., Catalyzed Dioctyl Phthalate Formation Using a Nanostructured Solid Acid Resin; American Institute of Chemical Engineers Journal, Jan. 2005, vol. 52, No. 1, pp. 418-421.
Kiss et al., Solid Acid Catalysts for Biodiesel Production—Toward Sustainable Energy; Adv. Synth. Catal. 2006, 348, 75-81.
Response to Non-Final Office Action in U.S. Appl. No. 11/744,693, filed Sep. 29, 2008.
U.S. Appl. No. 11/744,693, filed May 4, 2007, Elliott.
Office Action issued in U.S. Appl. No. 11/744,693 on Mar. 28, 2008.
Abreu et al. (2005, avail. online Dec. 2004) "New multi-phase catalystic systems based on tin compounds active for vegetable oil transesterification reaction," J. Molecular Catalysis A: Chemical 227:263-267.
Furuta et al. (2004) "Biodiesel fuel production with solid superacid catalysis in fixed bed reactor under atmospheric pressure," Catalysis Comm. 5:721-723.
Kiss et al. (Nov. 2006) "The heterogeneous advantage: biodiesel by catalytic reactive distillation," Topics Catalysis 40 (1-4) 141-150.
Jitputti et al. (Feb. 2006) "Transesterification of crude palm kernel oil and crude coconut oil by different solid acid catalysts," Chemical Engineering J. 116:61-66.
Karmee et al. (Feb. 2005) "Preparation of biodiesel from crude oil of *Pongamia pinnata*," Bioresource Technology 96:1425-1429.
Lopez et al. (Sep. 2005) Transesterification of triacetin with methanol on solid acid and base catalysts, Applied Catalysis A: General 295:97-105.
Lotero et al. (Jan. 2005) "Synthesis of Biodiesel via Acid Catalysis," Ind. Eng. Chem. Res., 44:5353-5363.
Mbaraka et al. (2003) "Organosulfonic acid-functionalized mesoporous silicas for the esterification of fatty acid," J. Catalysis 219:329-336.
Pouilloux et al. (1999) "Reaction of glycerol with fatty acids in the presence of ion-exchange resins Preparation of monoglycerides," J. Molecular Catalysis A: Chemical 149:243-254.
Sreeprasanth et al. (Sep. 2006) "Hydrophobic, solid acid catalysts for production of biofuels and lubricants," Applied Catalysis A: General 314:148-159.
Takagaki et al. (Jun. 2006) "Esterification of higher fatty acids by a novel strong solid acid," Catalysis Today 116:157-161.
Tesser et al. (Sep. 2005) "Kinetics of Oleic Acid Esterification with Methanol =in the Presence of Triglycerides," Ind. Eng. Chem. Res. 44:7978-7982.
Toda et al. (Nov. 2005) "Biodiesel made with sugar catalyst," Nature, 438:178.
Office Action in U.S. Appl. No. 11/744,693 mailed Jun. 11, 2009.
Response to Office Action filed in U.S. Appl. No. 11/744,693 on Dec. 11, 2009 including all items filed with that response.

* cited by examiner

METHOD OF MAKING ALKYL ESTERS

STATEMENT REGARDING FEDERALLY SPONSORED RESEARCH OR DEVELOPMENT

This invention was made, at least in part, with funding from the Department of Energy Contract No. DE-FG02-04ER86169, Accordingly, the U.S. government may have certain rights in the invention.

CROSS-REFERENCE TO RELATED APPLICATIONS

Not applicable.

BACKGROUND

1. Field of the Invention

This invention relates generally to the field of alkyl esters. More particularly, the invention relates to a method of making alkyl esters from low-cost feedstock.

2. Background of the Invention

Alkyl esters, including methyl ester or ethyl ester, also known as "biodiesel", are a renewable and clean burning alternative to conventional petroleum-derived diesel fuel. Biodiesel is made from a raw or used vegetable oil or animal fat, typically soybean oil or rapeseed oil. Because biodiesel is made from natural oil or fat sources, the alkyl esters typically comprise $C_{14}$ to $C_{18}$ fatty chains if derived from vegetable oil, and $C_{16}$ to $C_{22}$ fatty chains if derived from animal fat. Biodiesel can be combusted in diesel (combustion-ignition) engines either in pure form or as blended with petroleum-derived diesel fuel. Biodiesel provides the benefits of a renewable resource as well as providing lower sulfur emissions than petroleum diesel. Biodiesel is effectively a zero-sulfur emission fuel.

Alkyl esters can be produced from any vegetable oil source and can be made from the crude oil, or from oils that have been processed by filtration, refining, or other processing steps. Additionally, alkyl esters may be derived from various grades of vegetable oil including virgin oils, yellow grease (free fatty acid content of up to 15%) brown grease (flee fatty acid content of greater than 15%), or by-products of the edible oil refining process such as acidulated soap stock. Acidulated soap stock is typically made by reacting soap by-product from the vegetable oil refining process with sulfuric acid, and is composed of over 70% free fatty acid. Each grade of vegetable oil contains varying amounts of triglycerides, diglycerides, monoglycerides, free fatty acids, and glycerin, as well as other impurities. Suitable feedstocks include not only high quality refined vegetable oils, but lower grade oils such as degummed oil, once refined oil such as acidulated soybean soap stock, and animal fats such as tallow, poultry fats and used greases.

The feedstock costs of fuels contribute very significantly to the final cost of the fuel product. Hence, it is desirable to use lower-cost oil feedstocks that contain higher levels of free fatty acid. However, alkyl esters are commonly made by processes that require highly refined vegetable oils. For example, the base-catalyzed transesterification of triglycerides with an alcohol such as methanol is widely understood. In these processes, a homogeneous catalyst is used (one that dissolves into the feedstock mixture). Base catalyzed transesterification is preferred over acid catalyzed transesterification because the reaction rate for converting triglycerides to alkyl esters (and glycerin co-product) is much higher. Unfortunately, the transesterification processes cannot tolerate high levels of free fatty acid because soap by-product is produced, and complicates the product recovery and purification and irreversibly consumes a portion of the catalyst. Therefore base catalyzed processes typically require a highly refined vegetable oil feedstock that is considerably more expensive than lower grade unrefined oil feedstocks.

Consequently, there remains a need for in the art for methods of making alkyl esters using unrefined and low-cost feedstocks.

BRIEF SUMMARY

Methods of making alkyl esters are described herein. Generally, the method involves converting a glyceride source to a fatty acid composition and esterifying the fatty acid composition in the presence of a solid acid catalyst to make alkyl esters. The methods are capable of using raw, unprocessed, low-cost feedstocks to make alkyl esters. In addition, the methods incorporate the use of packed bed reactors, reactive distillation, and solid acid catalysts.

These and other needs in the art are addressed in one embodiment by a method of making alkyl esters comprising providing a glyceride source. The method further comprises converting the glyceride source to a fatty acid composition comprising free fatty acids and less than about 1% glyceride by mass. Additionally, the method comprises esterifying the fatty acid composition in the presence of a solid acid catalyst at a temperature ranging from about 70° C. to about 120° C. to produce alkyl esters, such that at least 85% of the free fatty acids are converted to alkyl esters.

In another embodiment, a method of making alkyl ester comprises providing a fatty acid composition and an alcohol. The fatty acid composition comprises flee fatty acids and less than about 1% glycerides by mass. The method also comprises combining the fatty acid composition and the alcohol to form a mixture. Moreover, the method comprises passing the mixture through at least one packed bed reactor at a temperature ranging from about 70° C. to about 120° C. containing a solid acid catalyst to produce alkyl esters such that at least 85% of the flee fatty acids are converted to alkyl esters.

In a further embodiment, a method of making alkyl ester comprises providing a glyceride source. The method additionally comprises passing a mixture of the glyceride source and water through at least one packed bed reactor containing a solid acid catalyst to form a fatty acid composition. Moreover, the method comprises esterifying the fatty acid composition in the presence of an acid catalyst to produce alkyl esters.

In yet another embodiment, a method of making alkyl esters comprises providing a fatty acid composition and an alcohol. The fatty acid composition comprises free fatty acids and no more than 1% glycerides by mass. The method further comprises combining the fatty acid composition and the alcohol to form a mixture. Additionally, the method comprises passing the mixture through a reactive distillation column containing a solid acid catalyst to produce alkyl esters.

By converting the oil or fat source into a fatty acid composition, a wide variety of low-cost feedstock materials may be used that cannot be used in a base-catalyzed transesterification process without significant pre-treatment and removal or reaction of free fatty acids prior to transesterification. Free fatty acids are not compatible with base-catalyzed processes because the flee fatty acids are converted to soap, which consumes catalyst and complicates alkyl ester product recovery horn glycerin.

The use of solid acid catalysts also offers several advantages. When a solid acid catalyst is used in conjunction with a packed bed reactor and contained within that reactor by a porous filter or other means, reactants can be pumped through this reactor and exit the reactor without any acid or base contamination. Thus, solid acid catalyst eliminates or greatly reduces the need to neutralize the products leaving their reactors. The solid acid catalyst may also be used for long periods of time without re-generation or without producing any salt waste streams associated with other alkyl ester processes.

The foregoing has outlined rather broadly the features and technical advantages of the present invention in order that the detailed description of the invention that follows may be better understood. Additional features and advantages of the invention will be described hereinafter. It should be appreciated by those skilled in the art that the concepts and the specific embodiments disclosed herein may be readily utilized as a basis for modifying or designing other structures for carrying out the same purposes of the present invention. It should also be realized by those skilled in the art that such equivalent constructions do not depart from the scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Figure 1:
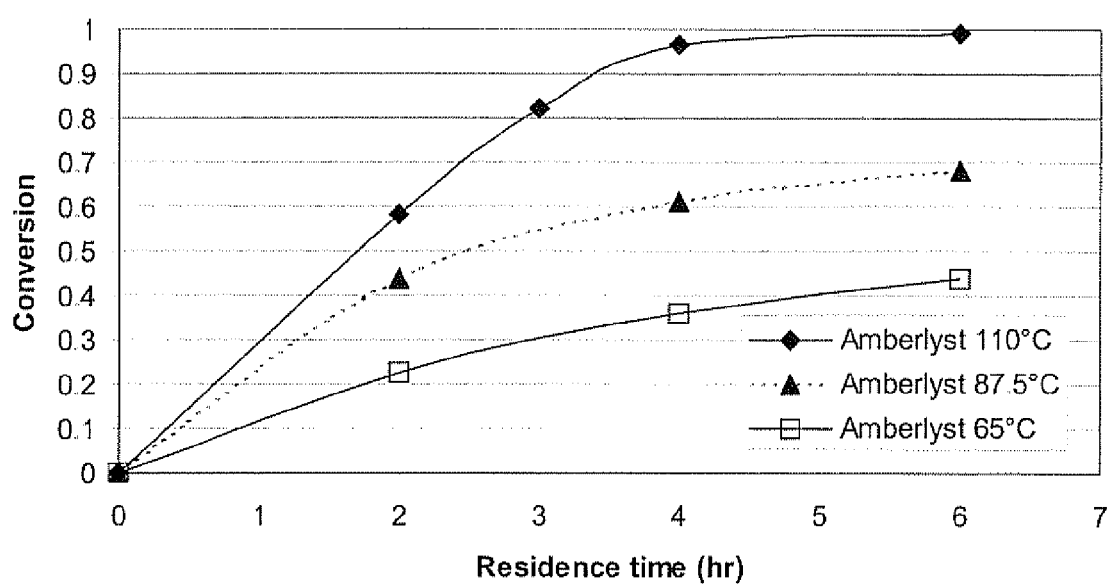
FIG. 1 is a plot of conversion of hexanoic acid to ethyl hexanoate in a catalytic packed bed reactor using Amberlyst-15.

Certain terms are used throughout the following description and claims to refer to particular system components. This document does not intend to distinguish between components that differ, in name but not function.

In the following discussion and in the claims, the terms "including" and "comprising" are used in an open-ended fashion, and thus should be interpreted to mean "including, but not limited to . . . ".

DETAILED DESCRIPTION OF THE PREFERRED EMBODIMENTS

The following reaction scheme illustrates an embodiment of a method for making alkyl esters:

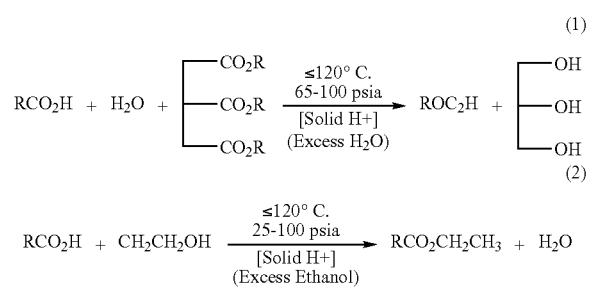

where R comprises any aliphatic group ranging from $C_6$ to $C_{22}$, more preferably from $C_{14}$ to $C_{22}$. In general, a glyceride source is converted to a fatty acid composition in which most of the glycerides have been converted to free fatty acids (Equation (1)). The fatty acid composition is then esterified in the presence of an acid catalyst to produce alkyl esters (Equation (2)).

In an embodiment, a glyceride source such as a vegetable oil or animal fat source is provided. Any suitable glyceride source may be used. Preferably, the glyceride source is a low-cost feedstock which has not been refined or processed. The glyceride source typically is comprised of triglycerides, but may also contain monoglycerides and diglycerides. Examples of suitable glyceride sources include without limitation, sunflower oil, rapeseed oil, soybean oil, vegetable oil, corn oil, canola oil, palm oil, olive oil, safflower oil, dryland mustard oil, or combinations thereof. The aforementioned oils may be raw or processed. In some embodiments, the glyceride source comprises animal fat or waste grease.

According to a preferred embodiment, converting the glycerides in the glyceride source into free fatty acids involves hydrolysis to from a fatty acid composition comprising glycerin and free fatty acids. However, any methods for converting glycerides into flee fatty acids that are known by those skilled in the art may be used. The flee fatty acids generally are purified by phase separation. Phase separation usually involves cooling the glycerin, thus allowing the glycerin to solidify and separating the free fatty acid from the solid glycerin phase. In another embodiment, glycerin is separated from the fatty acid composition in a continuous centrifuge or other separation device. Alternatively, the glycerin fraction may be left in the fatty acid composition used for esterification. The glycerin may then be removed after esterification of the fatty acid composition, The glyceride source is typically hydrolyzed in the presence of excess water. The water is preferably added in a ratio of about 5.0 moles of water to 1 mole of free fatty acid equivalent. For example, each triglyceride can produce 3 equivalents of flee fatty acids; therefore 15 moles of water may be used per in mole of triglyceride. Preferably, the hydrolysis takes place in the presence of an acid catalyst such as sulfuric acid. Other examples of acid catalysts include without limitation, hydrochloric acid, phosphoric acid, p-toluene sulfonic acids, etc. Thus, the glyceride source may be reacted with water in a mole ratio ranging from about 1:3 to about 1:15. In some embodiments, the hydrolysis utilizes a solid acid catalyst, thus eliminating the need to neutralize the product stream. The hydrolysis is preferably run at a temperature no more than about 200° C. and a pressure no more than about 500 psia. In other embodiments, the hydrolysis may be carried out at a temperature in the range of about 40° C. to about 120° C., and a pressure in the range of about 25 to about 100 psia.

In a particular embodiment, the hydrolysis is carried out using a solid acid catalyst in at least one packed bed reactor. Alternatively, the hydrolysis is carried out using a plurality of packed bed reactors. Typically, conditions in the packed bed reactor are about 120° C. and about 65 psia, however, the packed bed reactor may be operated at any temperatures and pressures suitable for hydrolysis.

The solid acid catalyst is preferably a polymeric ion-exchange resin or an inorganic solid acid. Examples of suitable polymeric ion-exchange resins include without limitation, Amberlyst® (Rolim and Haas CO., of Philadelphia, Pa.), and DOWEX® (Dow Chemical Co. of Midland, Mich.). Examples of suitable inorganic acid catalyst include without limitation, acidic zeolites (SUD Chemie of Glarus, Switzerland), silica-aluminas, metal oxides, mixed metal oxides, and clays.

The fatty acid composition formed after hydrolysis preferably contains at least about 50% free fatty acid by mass, preferably at least about 70% free fatty acid by mass, more preferably at least about 90% free fatty acid by mass, and still more preferably at least about 95% free fatty acid by mass. In certain embodiments, the majority of the glyceride in the glyceride source is converted to free fatty acids such that the fatty acid composition contains less than about 1% by mass glycerin. Examples of fatty acids that may be present in the fatty acid composition include without limitation, caprylic acid, capric acid, lauric acid, linoleic acid, acetic acid, butyric acid, lauric acid, myristic acid, palmitic acid, linolenic acid, stearic acid, oleic acid, arachidic acid, caproic acid, erucic acid, or combinations thereof. The fatty acid composition may contain glycerin and other impurities. Alternatively, most or all of the glycerin impurity is removed prior to direct esterification of the free fatty acids.

In another embodiment, converting the glycerides in the glyceride source into free fatty acids comprises generating acidulated soap stock. Generally, acidulated soap stock is generated from the by-products of refining. Ordinary vegetable oil refining typically involves removal of free fatty acids by saponification and separation. In saponification, melted oil is treated with a strong aqueous caustic soda solution to convert the free fatty acid present into soap. The oil and the alkali solution are thoroughly stirred together and sometimes warmed. The mixture is then allowed to separate.

The result is that the oil freed from fatty acid floats on top of a layer of soap, alkali solution, and other impurities, which is drawn off. The oil is then washed with water to remove any soap, alkali, and other impurities, whereupon it is ready for the decolorizing or deodorizing process. Other methods of refining known to those skilled in the art may be used.

The underlayer of soap and other impurities, which is drawn off from the oil, consists of solid matter mixed with some water. A large proportion of it is soap and it may be used to make low-grades of soap, hence it is known as "soap stock". In some embodiments of the invention, the soap stock is treated with a strong acid such as sulfuric acid so as to re-acidify the fatty acids contained in it. The re-acidified fatty acids then float to the surface and are skimmed off, forming the acidulated soap stock.

According to a preferred embodiment, the free fatty acids in a fatty acid composition are converted to alkyl esters by solid-acid catalyzed direct esterification. In an alternative embodiment, the fatty acid composition is directly esterified using a liquid acid catalyst such as sulfuric acid. The process for esterifying free fatty acids to alkyl esters generally involves contacting a fatty acid composition with excess alcohol over a solid acid catalyst at elevated temperatures and pressures. The alcohol is preferably methanol or ethanol. However, any suitable alcohol may be used, for example iso-propanol, n-butanol, 2-butanol or tert-butanol. Using methanol produces methyl esters and reaction water, while using ethanol produces ethyl esters and reaction water.

Because direct esterification reactions are reversible, it is preferable to use an excess of the alcohol. In preferred embodiments, the fatty acid composition is esterified with alcohol in the range of about 1.5 to about 10.0 free fatty acid equivalents, and more preferably from about 1.5 to about 5.0 free fatty acid equivalents. For example, 5.0 free fatty acid equivalents of alcohol means that 5 moles of alcohol are reacted with 1 mole of free fatty acid (i.e. 1 mole equivalent for the reaction and 4.0 mole equivalents excess.)

Any suitable solid acid catalysts may be used for the direct esterification reaction. Solid acid catalysts include without limitation, polymeric ion-exchange resins, nanostructured polymer acid catalysts, fluorinated polymer resins, inorganic acid catalysts, or combinations thereof. Examples of polymeric ion-exchange resins include without limitation, Amberlyst-™ or DOWEX-™. These ion exchange resins may be sulfonated crosslinked polystyrene in bead or powder form. Amberlyst and DOWEX are available in various grades. (Specific grades of Amberlyst recommended for esterification by Rohm and Hass include Amberlyst-15, -131, -16, and -36.) Fluorinated polymer resins, such as Nafion, are fluorinated polymers with sulfonic acid sites. Nanostructured polymer acid catalysts can be made by any methods known to one of ordinary skill in the art. Nanostructured polymer catalysts may be made by polymerizing self-assembled lyotropic liquid crystalline acid surfactants. Inorganic acid catalysts include sulfated zirconia, tungstated zirconia, supported Nafion on silica (SAC-13), zeolites, clays, silica-aluminas, and other metal oxides and mixed metal oxides.

In at least one embodiment, the fatty acid composition is esterified into alkyl esters by passing the reactants through a packed bed reactor or plug flow reactor containing a solid acid catalyst. In such an embodiment, the reactants (i.e. the fatty acid composition and alcohol) are generally pumped through a packed bed reactor in a continuous esterification process. There are several advantages to using solid acid catalysts in a packed bed reactor. Solid acids in general are characterized by acid sites which are immobilized on a solid supporting material. When a solid acid catalyst is used in a packed bed reactor and contained within that reactor by a porous filter or other means, reactants can be pumped through this reactor and exit the reactor without any acid or base contamination. Thus, a solid acid catalyst eliminates or greatly reduces the need to neutralize the products leaving their reactors. The solid acid catalyst may also be used for long periods of time without re-generation or without producing any salt waste streams. Additionally, utilizing a packed bed reactor may provide all the benefits of using a continuous process such as cost efficiency, quality control, etc.

The temperature in the reactor ranges preferably from about 40° C. to about 120° C., and more preferably from about 100° C. to about 120° C. The pressure preferably ranges from about 25 psia to about 100 psia, and more preferably from about 60 to about 100 psia. The residence time in the reactor is defined such that sufficient conversion of the free fatty acids into alkyl esters occurs. In typical embodiments, the residence time ranges from about 20 minutes to about 6 hours.

In further embodiments, the concentration of solid acid catalyst ranges from about 100 g/(liter of reactor volume) to about 3000 g/(liter of reactor volume). In some embodiments, the solid acid catalyst is ground and sieved into powders with an average diameter in the range of about 30 microns to about 60 microns. The preferred conversion of the free fatty acids to alkyl esters ranges from about 90% to about 100%, more preferably from about 99% to about 100%.

Esterification reactions are reversible and the equilibrium limited. Higher conversions (>99%) may be achieved by using multiple, or "staged" reactors. In an embodiment, alkyl ester may be produced by reacting a fatty acid composition near the equilibrium limit in at least one packed bed catalytic reactor, followed by removal of the reaction water, and then subsequently further reacted in one or more catalytic reactors. By removing the water, near complete conversion can be achieved. Alternatively, the process may comprise a packed bed reactor (to afford a composition near the equilibrium limit) followed by catalytic reactive distillation. Catalytic reactive distillation is known by those skilled in the art, and comprises a distillation column with a reactive section that contains a solid catalyst. The process operates continually, with continual removal of reaction water and recycle of alcohol. Thus, conversions beyond the equilibrium limit can be reached. Alternatively, the enriched fatty acid composition can be first reacted in a batch reactor for a period of time to afford some conversion to the alkyl ester, followed by additionally further converting it using either a continuous packed-bed reactor or a reactive distillation column. These processes are known as semi-continuous processes and are known by those skilled in the art. In another embodiment, alkyl ester can be produced entirely in a reactive distillation column. Reactive distillation is generally used when equilibrium limits the conversion, as in direct esterification. In an embodiment, butanol is used as the alcohol in the esterification. Without being limited by theory, butanol may be better suited for reactive distillation where water is a reaction byproduct because it has a higher boiling point than water and it easily separates from water in the liquid phase. This facilitates separation and recycle of the butanol back to the reactive column.

To further illustrate various illustrative embodiments of the present invention, the following examples are provided.

EXAMPLE 1

Palmitic acid (90%, Sigma-Aldrich) was combined with ethanol at a composition of 1 mole palmitic acid to 5 moles ethanol. Palmitic acid is a solid at room temperature and must be heated to about 60° C. to first melt it prior to mixing with hot ethanol, or alternatively the mixture can be combined and heated to about 50° C., at which point this amount of palmitic acid will dissolve in ethanol. The reactants were then heated and pumped through a packed bed catalytic reactor containing Amberlyst-15. The reactants were maintained at a temperature above 60° C. prior to entering the catalytic reactor. The temperature of the reactor was kept at a temperature of between 60° C. and 120° C. For each run an elevated pressure was maintained on the reactor and pre-reactor feed lines suitable to keep the ethanol and reaction by-product water in a liquid state.

Run 1 used a pre-reactor temperature of 80° C. and a reactor temperature of 120° C. (reactor contained a packed bed of Amberlyst-15) and a residence time in the packed bed reactor of 2 hours. The pressure was maintained at 70 psia (the bubble point pressure of ethanol at 120° C. is 62 psia). The acid value of the product that exited the catalytic reactor was determined by ASTM method D1980-87. The acid value (AV) of the product was 10.8 (mg KOH/g sample). The original acid value of the feedstock was 115.0, demonstrating that a majority of the free fatty acid was converted to the ethyl ester product in the reactor. The AV of 10.8 is very near the reported equilibrium concentration of free fatty acid for this esterification reaction. The product was a clear liquid at room temperature. The product from the reactor contained the ethyl palmitate ester, a small amount of palmitic acid, water and excess ethanol at a concentration approximately at equilibrium.

Run 2 was performed using the same palmitic acid and ethanol (1:5 mole:mole) feed and the same reactor and catalyst (Amberlyst-15) as run 1, but the residence time was 1 hour (at 120° C. and at a pressure of 70 psia). The product from run 2 had an acid value of 13.9, slightly above the equilibrium value.

Run 3 was performed using the same palmitic acid and ethanol (1:5 mole:mole) feed and the same reactor and catalyst (Amberlyst-15) as run 1, but the residence time was 6 hours at 110° C. and at a pressure of 70 psia. The product from run 3 had an acid value of 16.6. Thus a large fraction of the free fatty acids were converted to alkyl ester in one pass at these conditions.

Run 4 was performed using the same palmitic acid and ethanol (1:5 mole:mole) feed and the same reactor and catalyst (Amberlyst-15) as run 1, but the residence time was 4 hours (at 120° C. and at a pressure of 70 psia). The product from run 4 had an acid value of 10.8, indicating that the product from Run 1 (with a 2 hour residence time) is essentially at equilibrium.

TABLE 1

Conversion of palmitic acid (reacted with ethanol to form the ethyl ester) in a packed bed catalytic reactor using Amberlyst-15 for a single pass continuous process. Conversion values found by titrating according to ASTM method D1980-87.

| Residence time | Temperature/pressure | Conversion of palmitic acid |
|---|---|---|
| 1 hour | 120° C./70 psia | 87.9% |
| 2 hours | 120° C./70 psia | 90.6% |
| 4 hours | 120° C./70 psia | 90.6% |

EXAMPLE 2

Hexanoic acid is a liquid at room temperature and like longer chain free fatty acids found more commonly in vegetable oils and animal fats. It too can be reacted with alcohols over an acid catalyst to form alkyl esters. Ethyl hexanoate (the ester of ethanol and hexanoic acid) is an artificial flavoring, similar to orange oil, for food, beverages and perfumes.

Specifically, ethanol (anhydrous, Aldrich) and hexanoic acid (Aldrich) were mixed at a ratio of 5 moles alcohol to 1 mole acid. This liquid at room temperature was then pumped through a packed bed catalytic reactor containing Amberlyst-15 catalyst that was further ground and sieved to particles with diameters from 38 to 53 microns. The conversion of the hexanoic acid to ethyl hexanoate was determined by gas chromatography. This reaction was performed at the following temperature and residence time conditions and all experiments used a pressure of 65 psia: 2 hours and 110° C., 3 hours and 110° C., 4 hours and 110° C., 6 hours and 110° C., 2 hours and 87.5° C., 4 hours and 87.5° C., 6 hours and 87.5° C., 2 hours and 65° C., 4 hours and 65° C., and 6 hours and 65° C. The following table summarizes the conversion data obtained by gas chromatography. The same data are shown in graphical from in FIG. 1. Near complete conversion is possible for this reaction with a single pass at 110° C. with a residence time of 6 hours.

TABLE 2

Conversion of hexanoic acid (reacted with ethanol) at 65 psia in a packed bed catalytic reactor.

| Residence time (hr) | Amberlyst-15 at 110° C. | Amberlyst-15 at 87.5° C. | Amberlyst-15 at 65° C. |
|---|---|---|---|
| 0 hr | 0.0 | 0.0 | 0.0 |
| 2 hr | 0.58 | 0.44 | 0.23 |
| 3 hr | 0.82 | | |
| 4 hr | 0.96 | 0.61 | 0.36 |
| 6 hr | 0.99 | 0.68 | 0.44 |

EXAMPLE 3

Short-Chain Alkyl Esters using a Nanostructured Polymeric Catalyst

Figure 2:
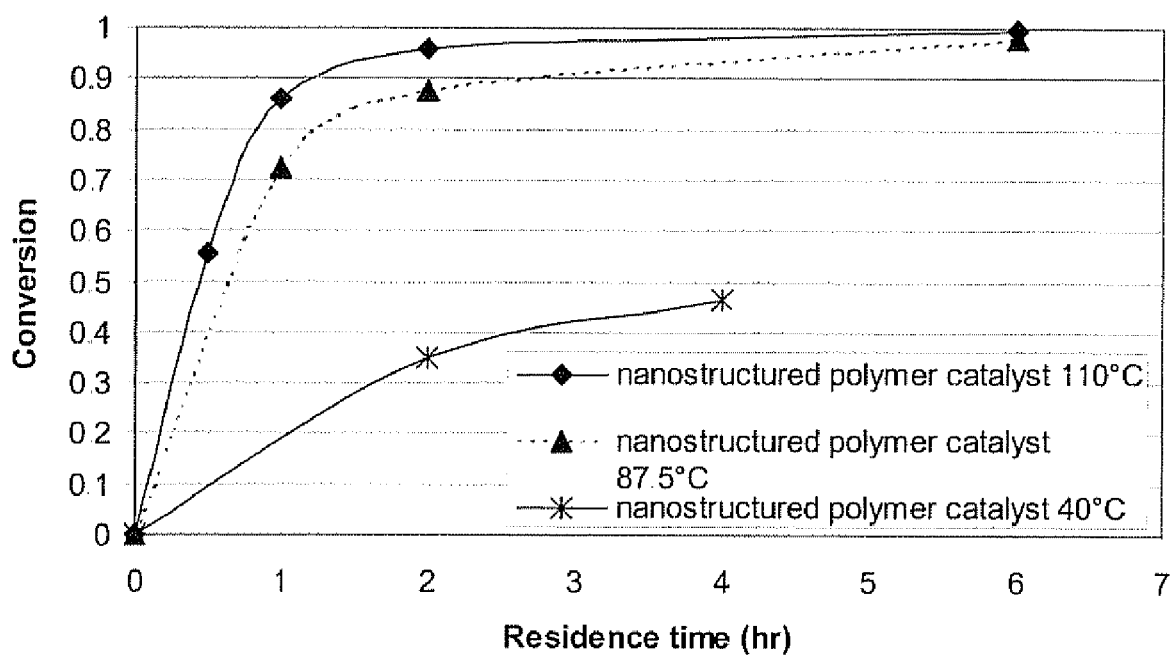
FIG. 2 is a plot of conversion of hexanoic acid to ethyl hexanoate in a catalytic packed bed reactor using a nanostructured solid acid polymer.

Nanoporous polymeric catalysts have demonstrated utility for acid catalyzed low-temperature reactions such as esterifications as described in Yanjie Xu, Douglas L. Gin, and Brian J. Elliott, "Catalyzed Dioctyl Phthalate Formation Using a Nanostructured Solid Acid Resin" *AIChE Journal*, Vol 52, no. 1 January 2005, herein incorporated by reference. Nanoporous polymer acid catalysts were prepared by the methods described by Xu et al. The ethyl-sulfonic acid tri-acrylate polymerizable surfactant was specifically prepared as described in Xu et al. (Xu, 2004), and were polymerized in the inverted hexagonal phase. In this case, structure-directing amino acid surfactant was not used as described, but a sample made entirely from the ethyl sulfonic acid surfactant, which had an inverted hexagonal phase mixed with some other liquid crystalline phase or phases, was used. These nanostructured catalysts were ground and sieved into powders with particle sizes of 38 to 53 microns in diameter. This reaction was performed at the following temperature and residence time conditions and all experiments used a pressure of 65 psia: 0.5 hours and 110° C., 1 hour and 110° C., 2 hours and 110° C., 6 hours and 110° C., 1 hour and 87.5° C., 2 hours and 87.5° C., 2 hours and 40° C., and 4 hours and 40° C. The following table summarizes the conversion data obtained by gas chromatography. The same data are shown in graphical from in FIG. 2. High conversions are possible for this reaction with a single pass at 110° C. with a residence time of 2 to 6 hours.

TABLE 3

Conversion of hexanoic acid (reacted with ethanol) at 65 psia in a packed bed catalytic reactor.

| Residence time (hr) | Nanostructured polymer catalyst at 110° C. | Nanostructured polymer catalyst at 87.5° C. | Nanostructured polymer catalyst at 65° C. |
|---|---|---|---|
| 0 hr | 0.0 | 0.0 | 0.0 |
| 0.5 hr | 0.56 | | |
| 1 hr | 0.86 | 0.73 | |
| 2 hr | 0.96 | 0.88 | 0.36 |
| 4 hr | | | 0.46 |
| 6 hr | 0.99 | | |

EXAMPLE 4

Converting Linoleic Acid into Alkyl Ester

Linoleic acid (65%, Fluka) was combined with ethanol at a composition of 1 mole linoleic acid to 5 moles ethanol (100 grams of anhydrous ethanol to 125 grams of linoleic acid composition). Linoleic acid is a liquid at room temperature and is miscible with ethanol. The reactants were heated and pumped through a packed bed catalytic reactor (a plug flow reactor) containing Amberlyst-15. The reactants were maintained at a temperature of 49° C. prior to entering the catalytic reactor. The temperature of the reactor was kept at 120° C. A pressure of 70 psia was maintained on the reactor and pre-reactor feed. The residence time in the packed bed reactor was either 1 or 2 hours. The acid value of the product that exited the catalytic reactor was determined by ASTM method D 1980-87. The acid value (AV) of the product using a 2 hour residence time was 10.7 (mgKOH/g sample), while the acid value of the product using a 1 hour residence time was 11.6. The original acid value of the feedstock was 121.2, demonstrating that a majority of the free fatty acid was converted to the ethyl ester product in the reactor. The product was a clear liquid at room temperature. The product from the reactor contained the ethyl linoleate ester, glycerin, a small amount of linoleic acid, water and excess ethanol at a concentration approximately at equilibrium.

TABLE 4

Conversion of linoleic acid (reacted with ethanol to form the ethyl ester) in a packed bed catalytic reactor using Amberlyst-15 for a single pass continuous process. Conversion values found by titrating according to ASTM method D1980-87

| Residence time | Temperature/pressure | Conversion of linoleic acid |
|---|---|---|
| 1 hour | 120° C./70 psia | 90.4% |
| 2 hours | 120° C./70 psia | 91.2% |

EXAMPLE 5

Converting Linoleic Acid into Alkyl Ester using a 1:2 Mole Ratio

Linoleic acid (65%, Flutka) was combined with ethanol at a composition of 1 mole linoleic acid to 2 moles ethanol (32 grams of anhydrous ethanol to 100 grams of linoleic acid composition). Linoleic acid is a liquid at room temperature and is miscible with ethanol. The reactants were heated and pumped through a packed bed catalytic reactor containing Amberlyst-15. The reactants were maintained at a temperature of 40° C. prior to entering the catalytic reactor. The temperature of the reactor was kept at 120° C., a pressure of 70 psia was maintained on the reactor and pre-reactor feed. The residence time in the packed bed reactor was either 1 or 3 hours. The acid value of the product that exited the catalytic reactor was determined by ASTM method D1980-87. The acid value (AV) of the product using a 3 hour residence time was 20.6 (mgKOH/g sample), while the acid value of the product using a 1 hour residence time was 28.0. The original acid value of the feedstock was 121.2. The product was a clear liquid at room temperature.

EXAMPLE 6

Converting Linoleic Acid into Alkyl Ester using a 1:5 Mole Ratio of Methanol Palmitic acid (90%, Sigma-Aldrich) can be combined with methanol at a composition of 1 mole palmitic acid to 5 moles methanol. Palmitic acid is a solid at room temperature and is heated to about 60° C. to first melt it prior to mixing with hot methanol. The products are then heated and pumped through a packed bed catalytic reactor containing Amberlyst-15. The reactants will be maintained at a temperature above 60° C. prior to entering the catalytic reactor. The temperature of the reactor will be kept at a temperature of between 60° C. and 120° C. An elevated pressure will be maintained on the reactor and pre-reactor feed lines suitable to keep the methanol and reaction by-product water in a liquid state. For example, at 120° C. a pressure greater than 93 psia will be used. 100 psia may also be suitable for this process.

EXAMPLE 7

Converting Linoleic Acid into Alkyl Ester using a Two-Staged Reactor Process Multi-staged reaction processes can be used to achieve product conversions higher than the equilibrium limitation. For example, the crude product from example 4, which was reacted in the packed bed catalytic reactor for 2 hours, was collected and heated to 110° C. for 30 minutes at ambient pressure to remove ethanol and water. The dried product, containing ethyl linoleate and unreacted linoleic acid, was mixed with ethanol at a mass ratio of 1 part ethanol to 1.25 parts of the ethyl linoleate/linoleic acid composition. This mixture was then processed again by pumping it over a packed bed reactor containing Amberlyst-15, with a residence time of 2 hours, a reactor temperature of 120° C., and a pressure of 70 psia. The acid value of the product exiting the reactor was 4.1 (which corresponds to 96.61% conversion of linoleic acid to ethyl linoleate).

Alternatively, a depressurized final reactor was used to finish the reaction by eliminating water in the presence of excess ethanol. For example the above prepared ethanol and ethyl linoleate/linoleate acid mixture from Example 4 was pumped over a packed bed reactor containing Amberlyt-15, with a residence time of 15 min, a reactor temperature of 125° C., and a pressure of 15 psia. The acid value of the product exiting the reactor was 1.7, which represents 98.6% conversion of the linoleic acid to the ethyl linoleate ester.

A distillation step can be used to further purify the product. Distillation of the product is expected to give an alkyl ester having at least 99% purity. Distillation can be used to separate the alkyl ester from unreacted fatty acids.

Reactive distillation can be used to further react the remaining free fatty acids while simultaneously purifying the alkyl ester. Reactive distillation is expected to give an alkyl ester having at least 99% purity (or less than 1% free fatty acid). A process using a packed bed reactor containing a solid acid catalyst to first provide at least 90% conversion of the fatty acids to alkyl esters followed by using a reactive distillation column containing a solid acid catalyst in the reaction zone with recycle of the alcohol is expected to give an alkyl ester having at least 99% purity.

Although the present invention and its advantages have been described in detail, it should be understood that various changes, substitutions and alterations may be made herein without departing from the spirit and scope of the invention as defined by the appended claims.

What is claimed is:

1. A method of making alkyl esters comprising:
    a) providing a fatty acid composition and an alcohol, wherein the fatty acid composition comprises free fatty acids and no more than 1% glycerides by mass;
    b) combining the fatty acid composition and the alcohol to form a mixture; and
    c) passing the mixture through at least one packed bed reactor at a temperature ranging from about 40° C. to about 120° C. containing sulfated zirconia to produce alkyl esters, such that at least 90% of the free fatty acids are converted to alkyl esters, wherein an elevated pressure is maintained in step (c) to keep the alcohol and by-product water in the liquid state and wherein the concentration of sulfated zirconia in the at least one packed bed reactor ranges from 100 g/(liter of reaction volume) to 3000 g/(liter of reaction volume), wherein providing the fatty acid composition comprises converting a glyceride source to the fatty acid composition comprising hydrolyzing the glyceride source with water in the presence of an acid catalyst and wherein (c) is a continuous process.

2. The method of claim 1, wherein the acid catalyst for hydrolyzing the glyceride source is a solid acid catalyst selected from the group consisting of polymer ion-exchange resins, acid zeolites, metal oxides, and combinations thereof.

3. The method of claim 1, wherein the acid catalyst for hydrolyzing the glyceride source is selected from the group consisting of sulfuric acid, hydrochloric acid, phosphoric acid, p-toluene sulfonic acid, and combinations thereof.

4. The method of claim 1, wherein the hydrolyzing of the glyceride source comprises passing a mixture of the glyceride source and water through a packed bed reactor containing a solid acid catalyst.

5. The method of claim 1, wherein the glyceride source to water mole ratio ranges from about 1:3 to about 1:15.

6. The method of claim 1, wherein the fatty acid composition comprises acidulated soap stock.

7. The method of claim 1 further comprising removing glycerin from the fatty acid composition after (b).

8. The method of claim 1 further comprising removing glycerin from the alkyl esters after (c).

9. The method of claim 1, wherein the glyceride source comprises sunflower oil, rapeseed oil, soybean oil, vegetable oil, corn oil, canola oil, palm oil, olive oil, safflower oil, dryland mustard oil, or combinations thereof.

10. The method of claim 1, wherein the glyceride source comprises animal fat.

11. The method of claim 1, wherein the fatty acid composition comprises more than about 90% free fatty acids by mass.

12. The method of claim 1, wherein (c) comprises esterifying the fatty acid composition at a pressure ranging from about 25 psia to about 100 psia.

13. The method of claim 1, wherein (c) comprises esterifying the fatty acid composition at a temperature ranging from about 70° C. to about 120° C.

14. The method of claim 1 further comprising reacting the mixture in a batch reactor before (c).

15. The method of claim 1 wherein (c) comprises passing the mixture through a plurality of packed bed reactors.

16. The method of claim 1, wherein the alcohol comprises n-butanol, 2-butanol, tert-butanol.

17. The method of claim 1 wherein the mixture passes through the at least one packed bed reactor with a residence time ranging from about 20 minutes to about 6 hours.

18. The method of claim 1, wherein the packed bed reactor is run at a pressure ranging from about 65 psia to about 100 psia.

19. The method of claim 1, wherein the mole ratio of free fatty acids to alcohol ranges from about 1:1.5 to about 1:5.

20. The method of claim 1 wherein the alcohol comprises ethanol or methanol.

21. The method of claim 4, wherein the solid acid catalyst for hydrolyzing the glyceride source is sulfated zirconia.

22. The method of claim 1 wherein the alcohol is ethanol or methanol.

23. The method of claim 1 wherein the alcohol is methanol.

24. The method of claim 1 wherein at least 99% of the free fatty acids are converted to alkyl esters.

* * * * *